US009476829B2

(12) United States Patent
Nagli et al.

(10) Patent No.: US 9,476,829 B2
(45) Date of Patent: Oct. 25, 2016

(54) METHOD AND APPARATUS FOR QUANTITATIVE ANALYSIS OF SAMPLES BY INDUCED PLASMA (LIP)

(75) Inventors: Lev Nagli, Petach Tikva (IL); Michael Gaft, Rishon LeZion (IL)

(73) Assignee: LASER DISTANCE SPECTROMETRY LTD., Petach Tikva (IL)

( * ) Notice: Subject to any disclaimer, the term of this patent is extended or adjusted under 35 U.S.C. 154(b) by 379 days.

(21) Appl. No.: 14/119,046

(22) PCT Filed: Jun. 7, 2012

(86) PCT No.: PCT/IL2012/000225
§ 371 (c)(1),
(2), (4) Date: Dec. 18, 2013

(87) PCT Pub. No.: WO2012/168938
PCT Pub. Date: Dec. 13, 2012

(65) Prior Publication Data
US 2014/0125965 A1    May 8, 2014

Related U.S. Application Data

(60) Provisional application No. 61/494,956, filed on Jun. 9, 2011.

(51) Int. Cl.
*G01N 21/00* (2006.01)
*G01N 21/59* (2006.01)
(Continued)

(52) U.S. Cl.
CPC ............. *G01N 21/59* (2013.01); *B07C 5/3427* (2013.01); *G01N 21/3103* (2013.01); *G01N 21/718* (2013.01); *G01N 2021/3125* (2013.01)

(58) Field of Classification Search
CPC .............. B07C 5/3427; G01N 2021/3125; G01N 21/3103; G01N 21/59; G01N 21/718
USPC ................................. 356/4.01, 432
See application file for complete search history.

(56) References Cited

U.S. PATENT DOCUMENTS 5,198,657 A    3/1993   Trost et al.
5,798,832 A    8/1998   Hnilica et al.
(Continued)

FOREIGN PATENT DOCUMENTS

| DE | 4426475      | 2/1995  |
|----|--------------|---------|
| RU | 2312325      | 12/2007 |
| WO | 2012/168938  | 12/2012 |

OTHER PUBLICATIONS

An English translation of an Office Action dated May 20, 2015, which issued during the prosecution of Russian Patent Application No. 2013158402.
(Continued)

*Primary Examiner* — Mark Hellner
(74) *Attorney, Agent, or Firm* — Sughrue Mion, PLLC

(57) ABSTRACT

A system for classifying moving materials in real time, the system including a laser pulse generator operative to generate at least first and second laser pulses which impinge on the same impingement location on the moving materials, the first and second laser pulses being separated in time by up to 10 microseconds; and an absorption detector operative to sense an absorption spectrum at the impingement location over a detection time duration of up to 20 nanoseconds following the second laser pulse.

19 Claims, 5 Drawing Sheets

(51) Int. Cl.
*G01N 21/31* (2006.01)
*G01N 21/71* (2006.01)
*B07C 5/342* (2006.01)

(56) References Cited

U.S. PATENT DOCUMENTS

| | | | |
|---|---|---|---|
| 5,847,825 A | 12/1998 | Alexander | |
| 6,657,721 B1 | 12/2003 | Palleschi | |
| 6,753,957 B1* | 6/2004 | Graft | G01N 21/718 356/318 |
| 6,788,407 B1 | 9/2004 | Higdon et al. | |
| 7,092,087 B2 | 8/2006 | Kumar | |
| 8,319,964 B2 | 11/2012 | Hahn | |
| 2005/0189503 A1 | 9/2005 | Jamieson et al. | |
| 2006/0114464 A1 | 6/2006 | Klingenberg et al. | |
| 2007/0085998 A1* | 4/2007 | Brestel et al. | G01J 3/2889 356/73 |

OTHER PUBLICATIONS

An International Search Report and a Written Opinion both dated Sep. 22, 2014 which issued during the prosecution of Applicant's PCT/IL14/50484.
Bernath, P. et al., "Laser Spectroscopy of CaBr." Journal of Molecular Spectroscopy, No. 88, (1981), pp. 175-193, [retrieved on Aug. 11, 2014]. Retrieved from the Internet <URL:http://bernath.uwaterloo.ca/media/5.pdf>.
Niki, H. et al., "Measurement technique of Boron Isotopic Ratio by Laser-induced Breakdown Spectroscopy", Journal of Nuclear Science and Technology, vol. 35., No. 1., pp. 34-39, Jan. 1998. [retrieved on Nov. 8, 2014], Retrieved from the Internet <URLhttp://www.tandfonline.com/doi/pdf/10.1080/18811248.1998.9733817>.
U.S. Appl. No. 61/494,956, filed Sep. 6, 2011.
M. Ribiere and B.G. Cheron, "Analysis of relaxing laser-induced plasmas by absorption spectroscopy: Toward a new quantitative diagnostic technique", Spectrochimica Acta part B, 65 ( 2010) 524-532.
M. Ribière, L. Mées, D. Allano, and B. G. Chéron, Evolutions in time and space of laser ablated species by dual-laser photoabsorption spectroscopy; Journal of Applied Physics, vol. 104, No. 4, p. 43302, Aug. 21, 2008.
P. K. Carroll and Gerry O'Sullivan, "X-UV Absorption Spectroscopy with Laser-Produced Plasmas; A Review", Physica Scripta. T34, 77-92, (1991).
William Whitty, John Costello, Eugene Kennedy, Christopher Moloney, Jean-Paul Mosnier, "Absorption spectroscopy of an expanding laser produced lithium plasma in the extreme ultraviolet using the Dual Laser Plasma technique", Applied Surface Science 127-129, 686-691 (1998).
Meighan, C Danson, L Dardis, C L S Lewis, A MacPhee, C McGuinness, R O'Rourke, W Shaikh, I C E Turcu and J T Costello, "Application of a picosecond laser plasma continuum light source to a dual-laser plasma photoabsorption experiment", J. Phys. B: At. Mol. Opt. Phys. 33 (2000) 1159-1168.
L. Nagli & M. Gaft & I. Gornushkin, "Comparison of single and double-pulse excitation during the earliest stage of laser induced plasma", Anal Bioanal Chem 400:3207-3216 (2011).
K. Song, Y.-I. Lee, J. Sneddon, "Applications of laser induced breakdown spectrometry", Appl. Spectrosc. Rev. 32 (1997) 183-235.
D. Cremers and L. Radziemski, "Handbook of Laser-Induced breakdown spectroscopy", (J. Wiley & Sons 2006).
David W. Hahn and Nicolo Omenetto, "Laser-Induced Breakdown Spectroscopy (LIBS), Part I: Review of Basic Diagnostics and Plasma-Particle Interactions: Still-Challenging Issues Within the Analytical Plasma Community", Applied Spectroscopy, vol. 64, No. 12, 2010, pp. 335-366.
A. Miziolek, V. Palleschi, I. Schechter, eds., "Laser Induced Breakdown Spectroscopy (LIBS)",. (Cambridge University Press ) Sep. 2006.
D.A. Rusak , B.C. Castle, B.W. Smith, J.D. Winefordner, "Fundamentals and applications of laser-induced breakdown spectroscopy", Crit. Rev. Anal. Chem. 27 (1997) 257-290.
L.J. Radziemski, "Review of selected analytical applications of laser plasmas and laser ablation", Microchem. J. 50 (1994) 218-234.
L.J. Radziemski, "From Laser to LIBS, the path of technology development", Spectrochim. Acta Part B 57 (2002) 1109-1113.
Pavel Yaroshchyk, Doug Body, Richard J.S. Morrison, Bruce L. Chadwick, "A semi-quantitative standard-less analysis method for laser-induced breakdown spectroscopy", Spectrochimica Acta Part B 61 (2006) 200-209.
An International Search Report and a Written Opinion both dated Sep. 27, 2012, which issued during the prosecution of Applicant's PCT/IL2012/000225.
An International Preliminary Report on Patentability dated Dec. 10, 2013, which issued during the prosecution of Applicant's PCT/IL2012/000225.
Reinhard Noll "Laser-Induced Breakdown Spectroscopy Fundamentals and Applications" Library of Congress Control No. 2011940321 Springer-Verlag Berlin Heidelberg 2012.

* cited by examiner

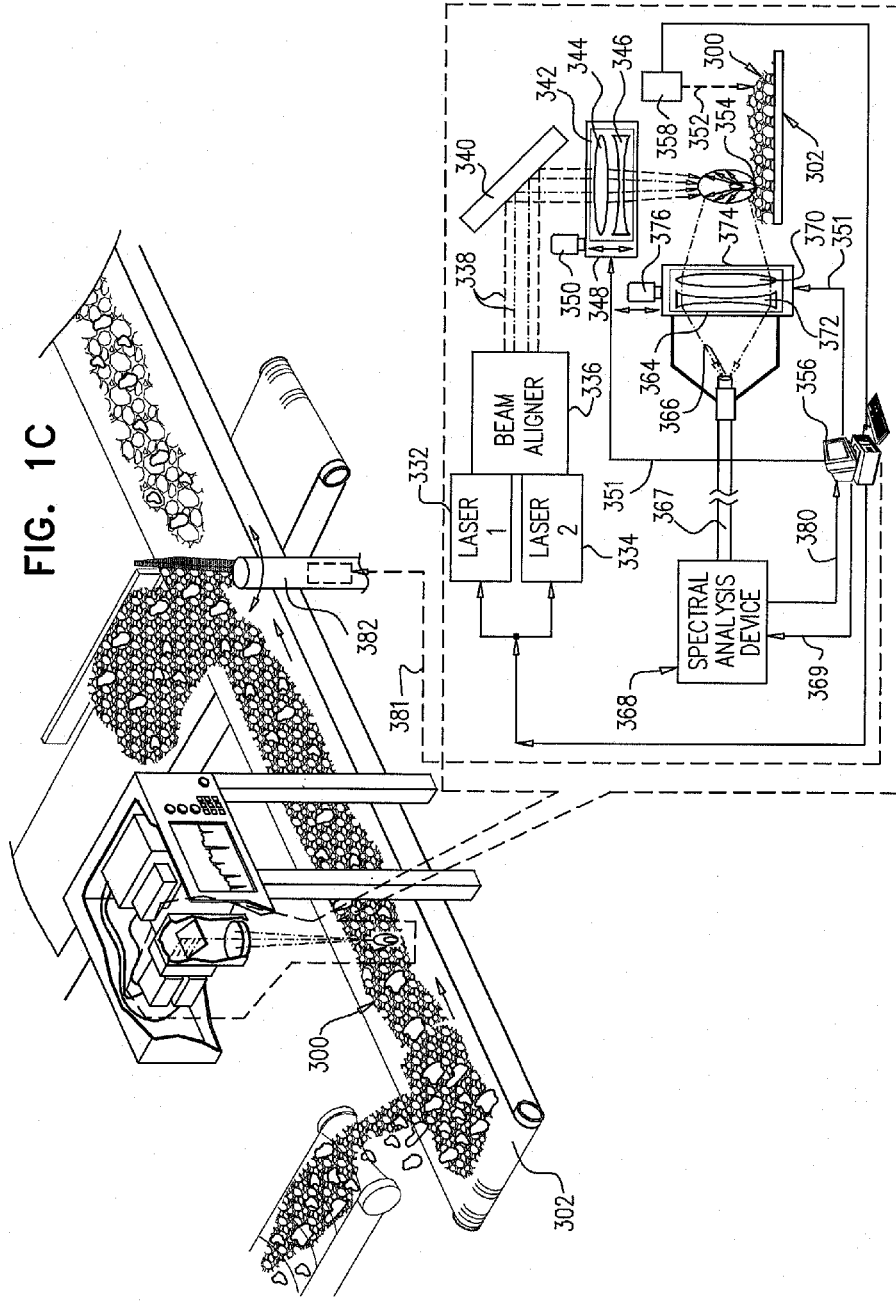

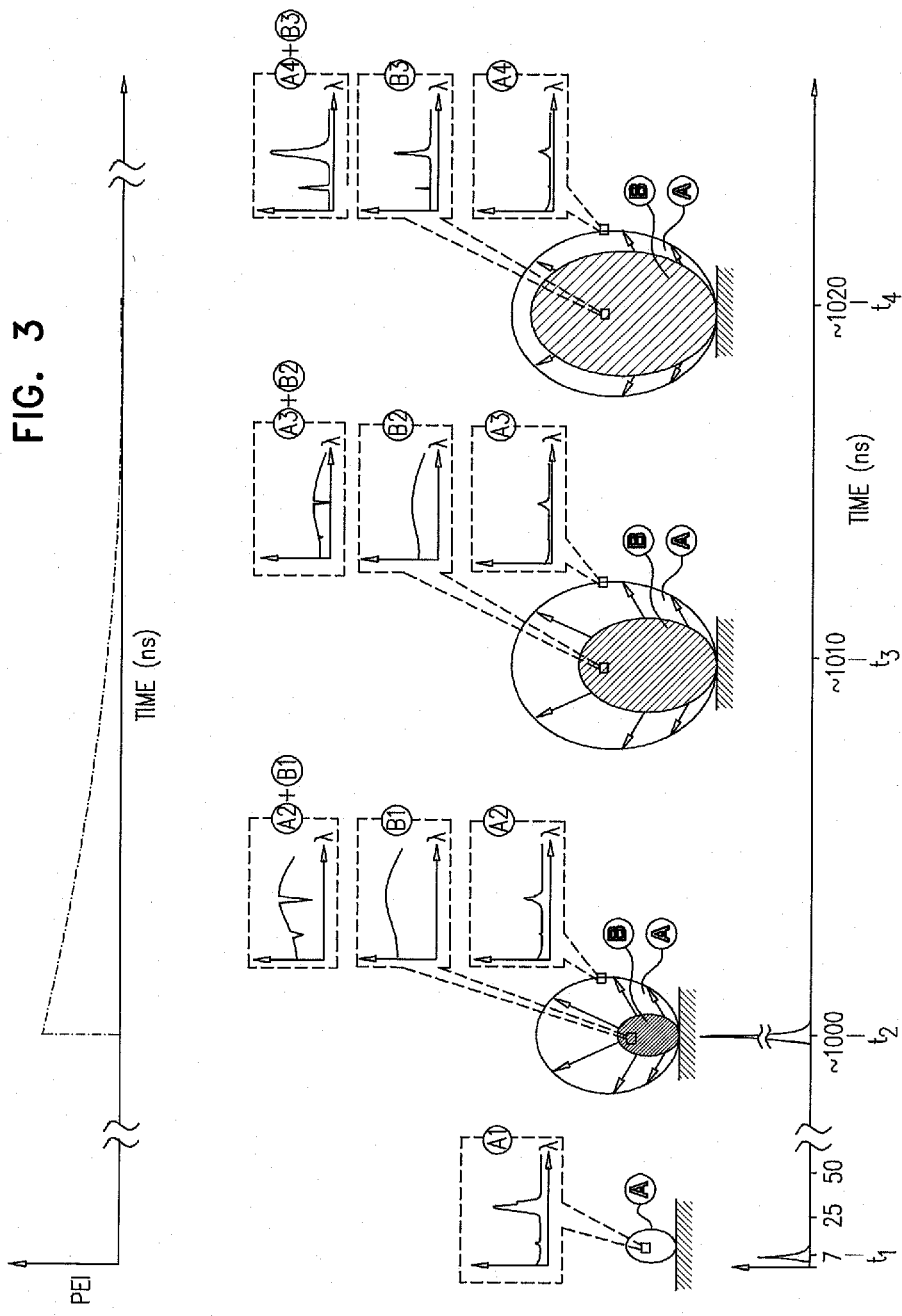

METHOD AND APPARATUS FOR QUANTITATIVE ANALYSIS OF SAMPLES BY INDUCED PLASMA (LIP)

CROSS REFERENCE TO RELATED APPLICATIONS

This is a National Stage of International Application No. PCT/IL2012/000225, filed Jun. 7, 2012, claiming priority from U.S. Patent Application No. 61/494,956, filed Jun. 9, 2011, the contents of all of which are incorporated herein by reference in their entirety.

REFERENCE TO RELATED APPLICATIONS

Reference is hereby made to U.S. Provisional Patent Application Ser. No. 61/494,956, filed Jun. 9, 2011 and entitled METHOD AND APPARATUS FOR QUANTITATIVE ANALYSIS OF SAMPLES BY LASER INDUCED PLASMA (LIP), the contents of which are hereby incorporated by reference and priority of which is hereby claimed pursuant to 37 CFR 1.78(a) (4) and (5)(i).

FIELD OF THE INVENTION

The present invention relates generally to classification of materials in real time.

BACKGROUND OF THE INVENTION

The following publications are believed to represent the current state of the art:

M. Ribiere and B. G. Cheron, "Analysis of relaxing laser induced plasmas by absorption spectroscopy; Toward a new quantitative diagnostic technique", Spectrochimica Acta Part B: Atomic Spectroscopy, vol. 65, no. 7, July, 2010, pp. 524-532;

M. Ribière, L. Méès, D. Allano, and B. G. Chèron, "Evolutions in time and space of laser ablated species by dual-laser photoabsorption spectroscopy"; Journal of Applied Physics, Vol. 104, No. 4, p. 43302, Aug. 21, 2008;

John Costello, Jean-Paul Mosnier, Eugene Kennedy, P. K. Carroll and Gerry O'Sullivan, "X-UV Absorption Spectroscopy with Laser-Produced Plasmas; A Review", Physica Scripta, Vol. T34, pp. 77-92, 1991;

William Whitty, John Costello, Eugene Kennedy, Christopher Moloney, Jean-Paul Mosnier, "Absorption spectroscopy of an expanding laser produced lithium plasma in the extreme ultraviolet using the Dual Laser Plasma technique", Applied Surface Science, vol. 127-129, May 1998, pp. 686-691;

O. Meighan, C. Danson, L. Dardis, C. L. S. Lewis, A. MacPhee, C. McGuinness, R. O'Rourke, W. Shaikh, I. C. E. Turcu and J. T. Costello, "Application of a picosecond laser plasma continuum light source to a dual-laser plasma photoabsorption experiment"; Journal of Physics B: Atomic, Molecular and Optical Physics, vol. 33, no. 6, Mar. 28, 2000, pp 1159-1164;

L. Nagli & M. Gaft & I. Gornushkin, "Comparison of single and double-pulse excitation during the earliest stage of laser induced plasma", Analytical and Bio-analytical Chemistry July 2011, 400:3207-3216;

K. Song, Y.-I. Lee and J. Sneddon, "Applications of laser induced breakdown spectrometry", Applied Spectroscopy Reviews, vol. 32, no. 3, 1997, pp. 183-235;

D. Cremers and L. Radziemski, Handbook of Laser-Induced breakdown spectroscopy; J. Wiley & Sons, April, 2006;

A. Miziolek, V. Palleschi and I. Schechter, eds., Laser Induced Breakdown Spectroscopy (LIBS), Cambridge University Press, September, 2006; and U.S. Pat. Nos. 6,753,957; 5,847,825; 6,657,721 and 7,092,087.

SUMMARY OF THE INVENTION

The present invention seeks to provide highly efficient and cost effective real time classification of materials while they are in motion, such as ores travelling along a conveyor in a mine.

There is thus provided in accordance with a preferred embodiment of the present invention a system for classifying moving materials in real time, the system including a laser pulse generator operative to generate at least first and second laser pulses which impinge on the same impingement location on the moving materials, the first and second laser pulses being separated in time by up to 10 microseconds; and an absorption detector operative to sense an absorption spectrum at the impingement location over a detection time duration of up to 20 nanoseconds following the second laser pulse.

Preferably, the absorption detector is operative to sense an absorption spectrum at the impingement location over a detection time duration of up to 10 nanoseconds following the second laser pulse. In accordance with a preferred embodiment of the present invention the absorption detector operative to sense an absorption spectrum at the impingement location over a detection time duration of up to 5 nanoseconds following the second laser pulse.

In accordance with a preferred embodiment of the present invention the system for classifying moving materials in real time also includes a real-time rangefinder measuring a current distance to the impingement location and a distance responsive laser beam focuser operative in response to an output from the real-time rangefinder for adjusting the focus of the laser pulses in real time to be focused on the impingement location notwithstanding varying heights of the materials. Alternatively, the system for classifying moving materials in real time also includes a real-time rangefinder measuring a current distance to the impingement location and a distance responsive absorption detection focuser operative for adjusting the focus of the absorption detector in real time to be focused on the impingement location notwithstanding varying heights of the materials.

Preferably, the system for classifying moving materials in real time also includes a distance responsive absorption detection focuser operative in response to the output from the real-time rangefinder for adjusting the focus of the absorption detector in real time to be focused on the impingement location notwithstanding varying heights of the materials.

In accordance with a preferred embodiment of the present invention the second laser pulse is generated at an energy level at least 5 times an energy level of the first laser pulse. Additionally, the second laser pulse is generated at an energy level 5-10 times an energy level of the first laser pulse.

Preferably, the system for classifying moving materials in real time also includes a beam aligner operative to align the first laser pulse and the second laser pulse.

In accordance with a preferred embodiment of the present invention the system for classifying moving materials in real time also includes a computer and a material directing gate, the computer operative to receive an output from the absorption detector and to provide a material directing output to the material directing gate.

There is also provided in accordance with another preferred embodiment of the present invention a method for classifying moving materials in real time including generating at least first and second laser pulses which impinge on the same impingement location on the moving materials, the first and second laser pulses being separated in time by up to 10 microseconds and sensing an absorption spectrum at the impingement location over a detection time duration of up to 20 nanoseconds following the second laser pulse.

Preferably, the sensing an absorption spectrum at the impingement location occurs over a detection time duration of up to 10 nanoseconds following the second laser pulse. In accordance with a preferred embodiment of the present invention the sensing an absorption spectrum at the impingement location occurs over a detection time duration of up to 5 nanoseconds following the second laser pulse.

In accordance with a preferred embodiment of the present invention the method also includes measuring a current distance to the impingement location and adjusting the focus of the laser pulses in real time to be focused on the impingement location notwithstanding varying heights of the materials. Alternatively or additionally, the method also includes adjusting the focus of the absorption detector in real time to be focused on the impingement location notwithstanding varying heights of the materials.

Preferably, the generating at least first and second laser pulses includes generating the second laser pulse at an energy level at least 5 times an energy level of the first laser pulse. In accordance with a preferred embodiment of the present invention the generating at least first and second laser pulses includes generating the second laser pulse at an energy level 5-10 times an energy level of the first laser pulse.

In accordance with a preferred embodiment of the present invention the generating at least first and second laser pulses includes aligning the first laser pulse and the second laser pulse.

Preferably, the method also includes providing a material directing output based on a function of the absorption spectrum.

BRIEF DESCRIPTION OF THE DRAWINGS

The present invention will be understood and appreciated more fully from the following detailed description, taken in conjunction with the drawings in which:

FIG. 1C is a simplified illustration of a system for classifying materials in real time while they are in motion in accordance with yet another preferred embodiment of the present invention;

FIG. 3 is a simplified illustration of aspects of the operation of the systems of FIGS. 1A, 1B and 1C.

DETAILED DESCRIPTION OF PREFERRED EMBODIMENTS

The present invention relates to a real time method and apparatus for quantitative analysis of solid, liquid and gas samples by Laser Induced Plasma (LIP), using calibration free atoms and ions absorption method.

Figure 1A:
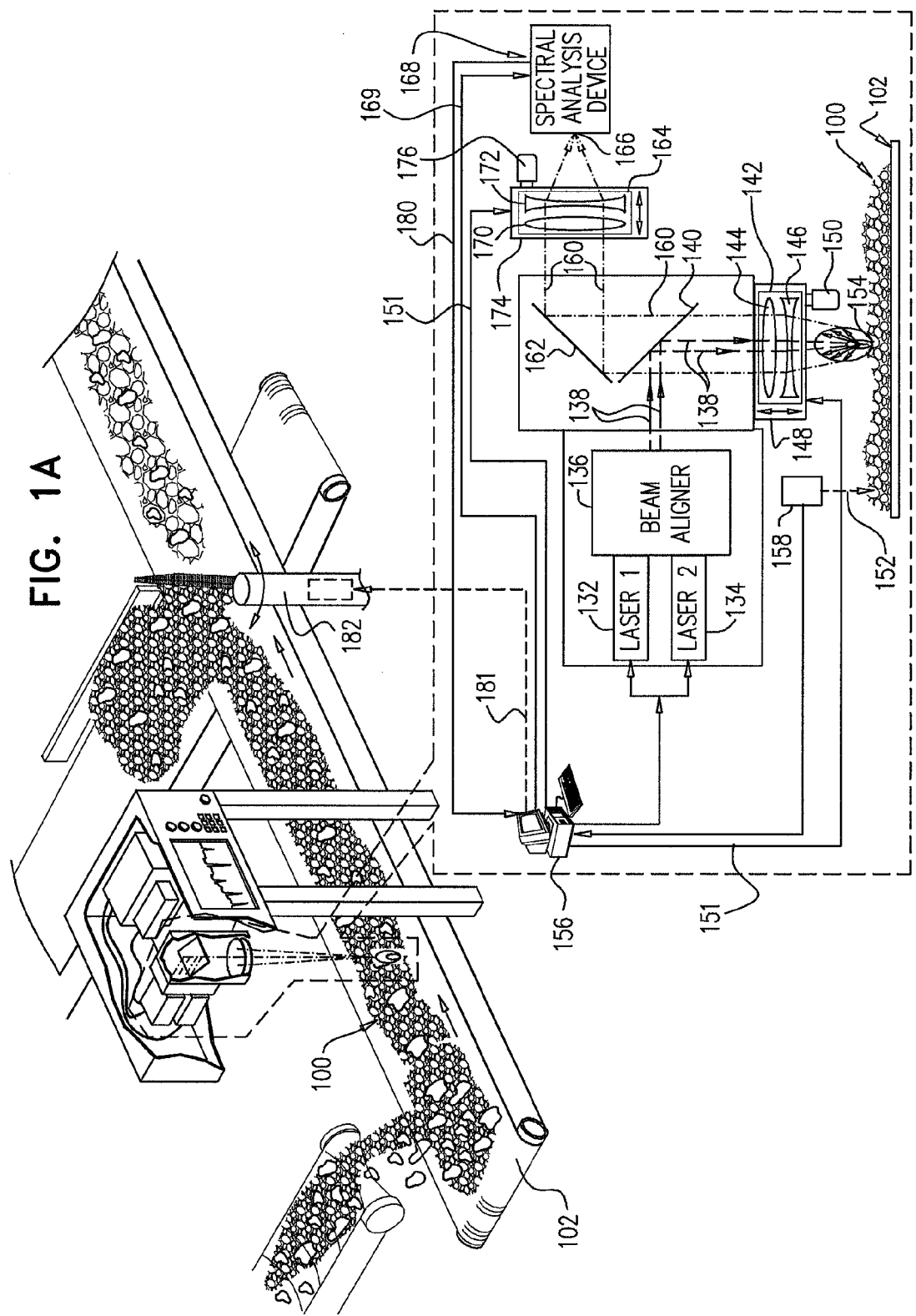
FIG. 1A is a simplified illustration of a system for classifying materials in real time while they are in motion in accordance with one preferred embodiment of the present invention.

Reference is now made to FIG. 1A, which is a simplified illustration of a system for classifying material in real time while they are in motion in accordance with one preferred embodiment of the present invention. As seen in FIG. 1A, bulk material 100, such as ore taken from a mine, recycled material, food or drugs on a manufacturing line, move along a conveyor 102, typically at a speed of 2-6 meters per second.

The present invention enables the material 100 to be classified in real time in accordance with its quantitative composition. Thus, in the example of ore taken from a mine, the quantity of specific elements in the ore may determine whether and how the ore is further processed. For example, in the case of iron ore, if the iron oxide content is more than a predetermined threshold, typically 60%, the ore is further processed and if the iron oxide content is less than the predetermined threshold the ore is discarded. In another example, if phosphate ore is being classified, ore having a magnesium oxide content exceeding a predetermined threshold, typically 2%, is discarded and ore having a magnesium oxide content which is less than the predetermined threshold is further processed.

In accordance with a preferred embodiment of the present invention, quantitative classification of the material 100 is achieved by employing a laser pulse generator operative to generate at least first and second laser pulses which impinge on the same impingement location on the material 100 when it is in motion, the first and second laser pulses being separated in time by up to 10 microseconds. An absorption detector, typically including a spectrometer, is operative to sense an absorption spectrum at the impingement location over a detection time duration of up to 20 nanoseconds following the second laser pulse. Alternatively, plural photodetectors, operative in the nanosecond range and each being associated with a different wavelength filter, may be employed.

Impingement of the first and second laser pulses on the material 100 produces mutually nested plasmas having a characteristic absorption spectrum over a time duration of most preferably up to about 10 ns following the second laser pulse, which absorption spectrum is clearly indicative of quantitative composition of the material 100 at the impingement location thereon, as described hereinbelow in detail with reference to FIGS. 2A-3.

As seen in FIG. 1A, the laser pulse generator preferably includes first and second lasers 132 and 134, typically Nd:YAG lasers each having an energy output of between 50 and 200 mJoule per pulse, which output via a beam aligner 136. The lasers 132 and 134 together with the beam aligner 136 are together commercially available from Quantel, 2 bis avenue du Pacifique, BP23 91 941, Les Ulis CEDEX, France, under the trade name TWINS BSL. The beam aligner 136 is operative to mutually align beams from lasers 132 and 134 which are at different physical locations so that the beams are precisely coaxial to within micron tolerances.

Typically, the lasers 132 and 134 output at a wavelength of 1064 nm. It is appreciated that other wavelengths may alternatively be used. It is also possible that lasers 132 and 134 may operate at different wavelengths. Normally, lasers 132 and 134 operate at different output energy levels, with the second laser 134, which produces the second laser pulse, operating at an energy level which is 5-10 times higher than the energy level of the first laser 132, which produces the first laser pulse. As a theoretical alternative, a single laser could be used, if such a laser could produce two laser pulses within 10 microseconds of each other.

Coaxial beam outputs 138 of beam aligner 136 are preferably supplied to a dielectric mirror 140, such as a Y—Nd:YAG Laser Mirror, commercially available from CVI Melles Griot, 200 Dorado Place SE, Albuquerque, NM 87123 USA, which is reflective for the coaxial beam outputs 138 and transparent to radiation received from plasmas created on the material 100 by impingement of the first and second pulses thereon and which reflects the coaxial beam outputs 138 onto an optical module 142, typically comprising first and second lenses 144 and 146, whose characteristics are as follows: F1=+80 mm–216 mm, D1=50 mm and F2=+108 mm–52 mm, D2=50 mm.

Lenses 144 and 146 are preferably mounted on a variable distance mounting assembly 148 including a linear motor 150, which enables the position of the lenses 144 and 146 as well as the distance between the lenses 144 and 146 to be varied in response to a control signal 151 based on a material height input 152. Material height input 152 represents the height of a beam focus location 154 of the coaxial output beams 138 on the material 100.

A computer 156 preferably governs the timing and other characteristics of the operation of first and second lasers 132 and 134 in order to provide desired timing and other operational characteristics of the corresponding first and second laser pulses and also provides control signal 151 in response to material height input 152 from a height sensor 158, such as an ultrasonic distance measuring device, for example a mic +130/IU/TC, commercially available from Microsonic GmbH of Hauert 16, 44227, Dortmund, Germany, or a laser rangefinder, such as an LDM 41/42 A, commercially available from ASTECH Angewandte Sensortechnik GmbH, Schonenfahrerstr. 5, D-18055, Rostock, Germany.

Optical module 142 is operative to focus the coaxial beam outputs 138 at the beam focus location 154 so as to preferably define a beam focus location having a diameter of approximately 300 microns. The beam focus location 154 is considered to be identical to the impingement locations of each of the first and second laser beams on the material 100, it being appreciated that a minor shift of up to about 10 microns in the impingement locations of the first and second beams on the material 100 will exist due to movement of the material 100 on the conveyor 102 between the times of the first and second laser pulse impingements. Impingement locations having a mutual center shift of no more than about 10 microns are considered to be the same impingement location.

Radiation from plasmas created on the material 100 by impingement of the first and second pulses thereon is partially collected by optical module 142, which collimates it into a collected radiation beam 160, which preferably passes through dielectric mirror 140 and impinges on a folding mirror 162, which in turn directs the collected radiation beam 160 onto a collected radiation focusing optical module 164. The optical module 164 focuses the collected radiation beam on a radiation collection location 166 of a spectral analysis device 168, such as a Shamrock SR-303i-A spectrometer combined with a fast Andor ICCD camera DH720-25F-03, commercially available from Andor Technology plc., 7 Millennium Way, Springvale Business Park, Belfast, BT12 7AL, United Kingdom. The ICCD camera preferably has a gating window whose opening duration is preferably governed by a control signal 169 from computer 156.

The optical module 164 preferably comprises first and second lenses 170 and 172 whose characteristics are as follows: F1=+70 mm–116 mm, D1=50 mm and F2=+80 mm–52 mm, D2=50 mm.

Lenses 170 and 172 are preferably mounted on a variable distance mounting assembly 174 including a linear motor 176, which enables the position of the lenses 170 and 172, as well as the distance between the lenses 170 and 172, to be varied by control signal 151 from computer 156.

Figure 2A:
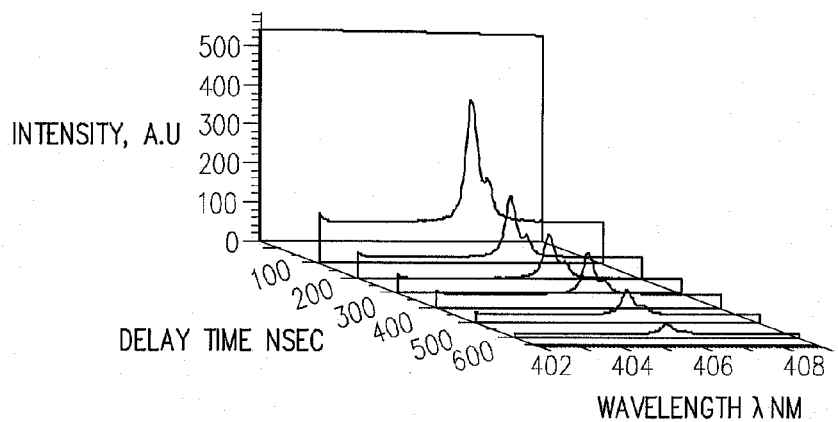
FIGS. 2A, 2B & 2C are a series of three, 3-dimensional intensity graphs, taken respectively at time periods t=0-900 ns, t=1000-1010 ns and t=1020-3000 ns which are characteristic of analysis of lead ore in accordance with a preferred embodiment of the present invention.
Figure 2B:
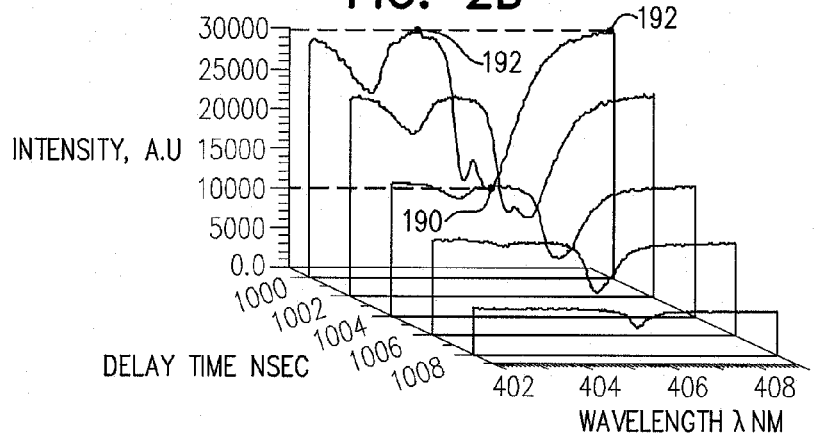
Figure 2C:
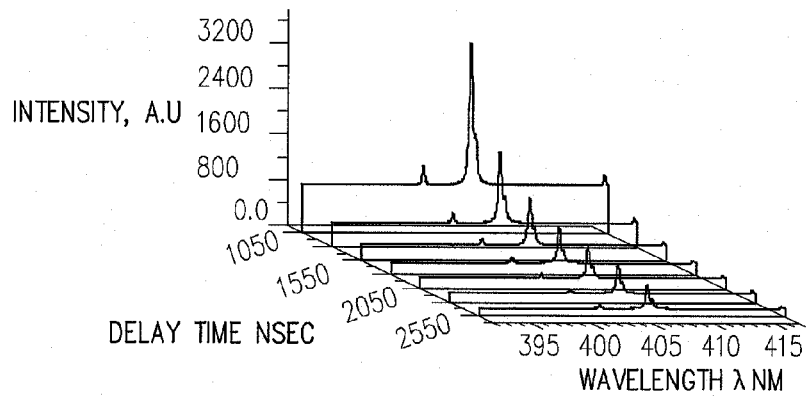

A spectral analysis output 180, typically as shown in FIGS. 2A-2C, from spectral analysis device 168, is preferably supplied to computer 156. FIGS. 2A-2C are a series of three, 3-dimensional intensity graphs, taken respectively at time periods t=0-900 ns, t=1000-1010 ns and t=1020-3000 ns, which are characteristic of analysis of lead ore in accordance with a preferred embodiment of the present invention. Each graph shows emission intensity as a function of both wavelength and time.

Computer 156 typically performs the following computational functions:

1. Calculates the Optical Density (O.D.) which is the logarithm (log) of the inverse intensity ratio between the minimum and the baseline adjacent thereto for each minimum in an intensity graph that represents an element of interest. For the purposes of illustration, reference is made to an intensity graph taken at t=1000 ns seen in FIG. 2B. The minimum is here designated by reference numeral 190 and the adjacent baseline is here designated by reference numeral 192. The intensity at the minimum 190 in this example is seen to be 10,000 while the intensity at the baseline 192 is seen to be 30,000. Thus the inverse of the ratio between the minimum and the baseline adjacent thereto is 3.0. The O.D. of the absorption at the wavelength which represents the specific element, here lead, is log 3 which equals 0.48.

It is a particular feature of the present invention that it employs the fact that the O.D. of the absorption spectrum at a wavelength which represents a given element is directly and linearly related to the quantitative concentration of the element, here lead, in the material 100. The linear relationship is preferably represented as follows:

$$N_i = \frac{2.3}{l\sigma_i}OD_i$$

where $N_i$ is the concentration for an element designated by "i", l is the difference in the radius of the diameters of the plasma plumes created by impingement of the respective first and second laser beams and is typically 400 microns at t=1000 ns (FIGS. 2B & 3) and $\sigma_i$ is the absorption cross section given by the expression:

$$\sigma_i = A_{21}\frac{1}{8\pi}\lambda_{0i}^2\frac{g_2}{g_1}$$

where $A_{21}$ is the Einstein coefficient for spontaneous emission for a specific energy level transition corresponding to the central wavelength, $\lambda_{0i}$ and $g_1$, $g_2$ are known constants representing the statistical weight of lower and upper energy levels to which the transition corresponds.

Referring to FIGS. 2A-2C, it is appreciated that a comparison of these graphs shows that absorbance is indicated only at and immediately following impingement of the second laser pulse on the material 100, typically at t=1000 ns, and not prior thereto, and not at a time t=1020 ns or more thereafter.

It is a particular feature of the present invention that the concentration calculated by computer 156 based on the sensed absorption at one or more wavelength characteristic of an element of interest is employed directly, and without the need for any calibration, to provide a material directing output to a material directing gate 182, which physically directs the material 100 in one of at least two directions depending on the quantitative composition thereof.

Figure 1B:
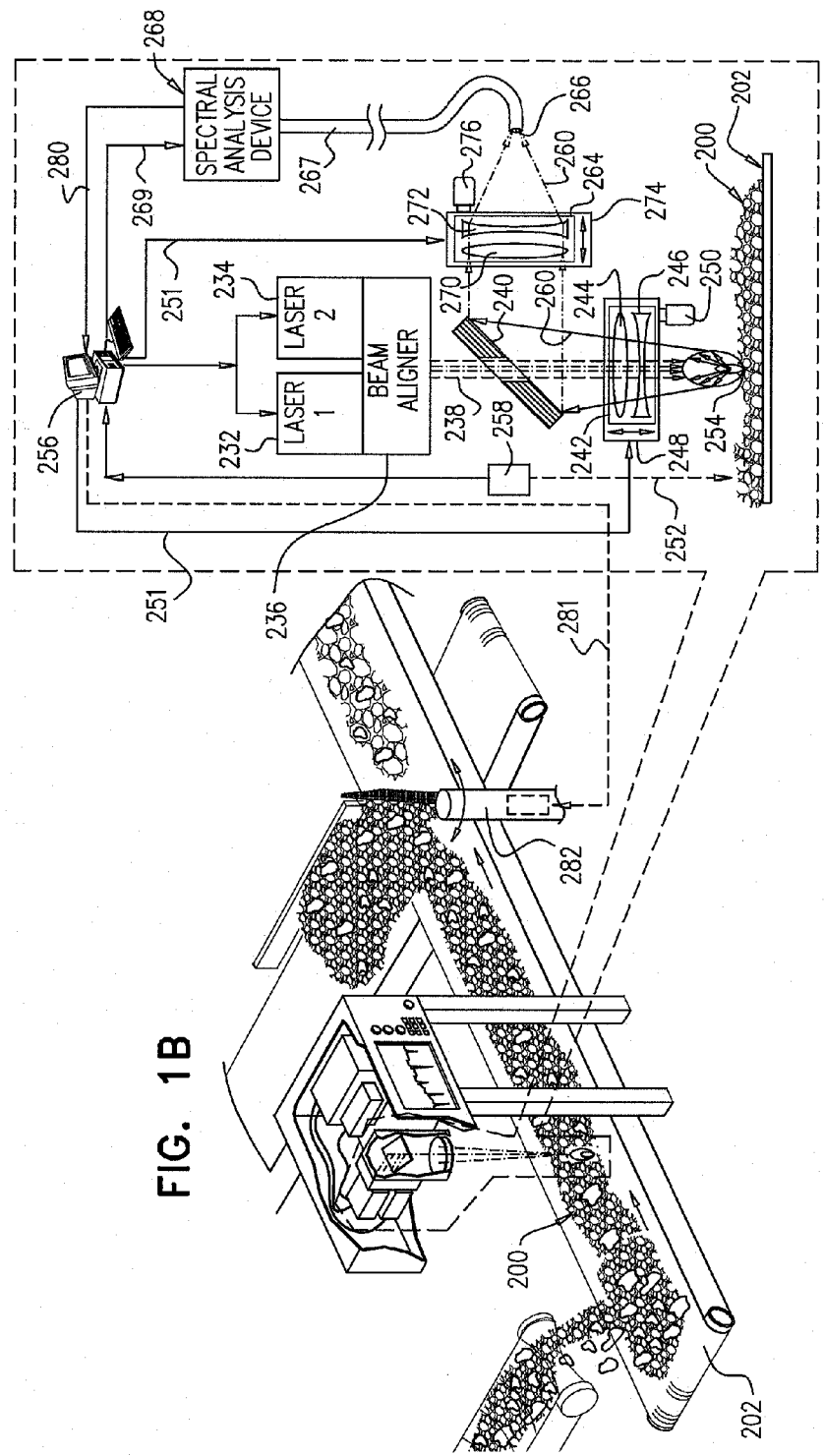
FIG. 1B is a simplified illustration of a system for classifying materials in real time while they are in motion in accordance with another preferred embodiment of the present invention.

Reference is now made to FIG. 1B, which is a simplified illustration of a system for classifying materials in real time while they are in motion in accordance with another preferred embodiment of the present invention. As seen in FIG. 1B, materials 200, such as ore taken from a mine, recycled materials, food or drugs on a manufacturing line, move along a conveyor 202, typically at a speed of 2-6 meters per second.

The present invention enables the materials 200 to be classified in real time in accordance with their quantitative composition. Thus, in the example of ore taken from a mine, the quantity of specific elements in the ore may determine whether and how the ore is further processed. For example, in the case of iron ore, if the iron oxide content is more than a predetermined threshold, typically 60%, the ore is further processed and if the iron oxide content is less than the predetermined threshold the ore is discarded. In another example, if phosphate ore is being classified, ore having a magnesium oxide content exceeding a predetermined threshold, typically 2%, is discarded and ore having a magnesium oxide content which is less than the predetermined threshold is further processed.

In accordance with a preferred embodiment of the present invention quantitative classification of materials 200 is achieved by employing a laser pulse generator operative to generate at least first and second laser pulses which impinge on the same impingement location on the materials 200 when they are in motion, the first and second laser pulses being separated in time by up to 10 microseconds. An absorption detector, typically including a spectrometer, is operative to sense an absorption spectrum at the impingement location over a detection time duration of up to 20 nanoseconds following the second laser pulse. Alternatively, plural photodetectors, operative in the nanosecond range and each being associated with a different wavelength filter, may be employed.

Impingement of the first and second laser pulses on materials 200 produces mutually nested plasmas having a characteristic absorption spectrum over a time duration of most preferably up to about 10 ns following the second laser pulse, which absorption spectrum is clearly indicative of quantitative composition of materials 200 at the impingement location thereon, as described hereinbelow in detail with reference to FIGS. 2A-3.

As seen in FIG. 1B, the laser pulse generator preferably includes first and second lasers 232 and 234, typically Nd:YAG lasers each having an energy output of between 50 and 200 mJoule per pulse, which output via a beam aligner 236. The lasers 232 and 234 together with the beam aligner 236 are together commercially available from Quantel, 2 bis avenue du Pacifique, BP23 91 941, Les Ulis CEDEX, France, under the trade name TWINS BSL. The beam aligner 236 is operative to mutually align beams from lasers 232 and 234 which are at different physical locations so that the beams are precisely coaxial to within micron tolerances.

Typically, the lasers 232 and 234 output at a wavelength of 1064 nm. It is appreciated that other wavelengths may alternatively be used. It is also possible that lasers 232 and 234 may operate at different wavelengths. Normally, lasers 232 and 234 operate at different output energy levels, with the second laser 234, which produces the second laser pulse, operating at an energy level which is 5-10 times higher than the energy level of the first laser 232, which produces the first laser pulse. As a theoretical alternative, a single laser could be used, if such a laser could produce two laser pulses within 10 microseconds of each other.

Coaxial beam outputs 238 of beam aligner 236 are preferably directed through an aperture formed in a metallic mirror 240, such as an NT47-117 mirror, commercially available from Edmund Optics Inc., 101 East Gloucester Pike, Barrington, N.J. 08007-1380 USA, onto an optical module 242, typically comprising first and second lenses 244 and 246 whose characteristics are as follows: F1=+80 mm−216 mm, D1=50 mm and F2=+108 mm−52 mm, D2 50 mm.

Lenses 244 and 246 are preferably mounted on a variable distance mounting assembly 248 including a linear motor 250, which enables the position of the lenses 244 and 246, as well as the distance between the lenses 244 and 246, to be varied in response to a control signal 251 based on a material height input 252. Material height input 252 represents the height of a beam focus location 254 of the coaxial output beams 238 on the materials 200.

A computer 256 preferably governs the timing and other characteristics of the operation of first and second lasers 232 and 234 in order to provide desired timing and other operational characteristics of the corresponding first and second laser pulses and also provides control signal 251 in response to material height input 252 from a height sensor 258, such as an ultrasonic distance measuring device, for example a mic +130/IU/TC, commercially available from Microsonic GmbH of Hauert 16, 44227, Dortmund, Germany, or a laser rangefinder, such as an LDM 41/42 A, commercially available from ASTECH Angewandte Sensortechnik GmbH, Schonenfahrerstr. 5, D-18055, Rostock, Germany.

Optical module 242 is operative to focus the coaxial beam outputs 238 at the beam focus location 254 so as to preferably define a beam focus location having a diameter of approximately 300 microns. The beam focus location 254 is intended to be identical to the impingement location of each of the first and second laser beams on the materials 200, it being appreciated that a minor shift of up to about 10 microns in the impingement location on the materials 200 will exist due to movement of the materials 200 on the conveyor 202 between the times of the first and second laser pulse impingements. Impingement locations having a mutual center shift of no more than about 10 microns are considered to be the same impingement location.

Radiation from plasmas created on the materials 200 by impingement of the first and second pulses thereon is partially collected by optical module 242, which collimates it into a collected radiation beam 260 which preferably is reflected by mirror 240 onto a collected radiation focusing optical module 264, which focuses the collected radiation beam 260 on a radiation collection fiber optic end 266 of an optical fiber 267 of a spectral analysis device 268, such as a Shamrock SR-303i-A spectrometer combined with a fast Andor ICCD camera DH720-25F-03, commercially available from Andor Technology plc., 7 Millennium Way, Springvale Business Park, Belfast, BT12 7AL, United Kingdom. The ICCD camera preferably has a gating window whose opening duration is preferably governed by a control signal 269 from computer 256.

The optical module 264 preferably comprises first and second lenses 270 and 272 whose characteristics are as follows: F1=+70 mm–116 mm, D1=50 mm and F2=+80 mm–52 mm, D2=50 mm.

Lenses 270 and 272 are preferably mounted on a variable distance mounting assembly 274 including a linear motor 276, which enables the position of the lenses 270 and 272 as well as the distance between the lenses 270 and 272 to be varied by control signal 251 from computer 256.

A spectral analysis output 280, typically as shown in FIGS. 2A-2C, from spectral analysis device 268 is preferably supplied to controller 256. FIGS. 2A-2C are a series of three, 3-dimensional intensity graphs, taken respectively at time periods t=0-900 ns, t=1000-1010 ns and t=1020-3000 ns, which are characteristic of analysis of lead ore in accordance with a preferred embodiment of the present invention. Each graph shows emission intensity as a function of both wavelength and time.

Computer 256 typically performs the following computational functions:

1. Calculates the Optical Density (O.D.) which is the logarithm (log) of the inverse intensity ratio between the minimum and the baseline adjacent thereto for each minimum in an intensity graph that represents an element of interest. For the purposes of illustration, reference is made to an intensity graph taken at t=1000 ns seen in FIG. 2B. The minimum is here designated by reference numeral 190 and the adjacent baseline is here designated by reference numeral 192. The intensity at the minimum 190 in this example is seen to be 10,000 while the intensity at the baseline 192 is seen to be 30,000. Thus the inverse of the ratio between the minimum and the baseline adjacent thereto is 3.0. The O.D. of the absorption at the wavelength which represents the specific element, here lead, is log 3 which equals 0.48.

It is a particular feature of the present invention that it employs the fact that the O.D. of the absorption spectrum at a wavelength which represents a given element is directly and linearly related to the quantitative concentration of the element, here lead, in the materials 200. The linear relationship is preferably represented as follows:

$$N_i = \frac{2.3}{l\sigma_i} OD_i$$

where $N_i$ is the concentration for an element designated by "i", l is the difference in the radius of the diameters of the plasma plumes created by impingement of the respective first and second laser beams and is typically 400 microns at t=1000 ns (FIGS. 2B & 3) and $\sigma_i$ is the absorption cross section given by the expression:

$$\sigma_i = A_{21} \frac{1}{8\pi} \lambda_{0i}^2 \frac{g_2}{g_1}$$

where $A_{21}$ is the Einstein coefficient for spontaneous emission for a specific energy level transition corresponding to the central wavelength, $\lambda_{0i}$ and $g_1$, $g_2$ are known constants representing the statistical weight of lower and upper energy levels to which the transition corresponds.

Referring to FIGS. 2A-2C, it is appreciated that a comparison of these graphs shows that absorbance is indicated only at and immediately following impingement of the second laser pulse on the materials 200, typically at t=1000 ns, and not prior thereto, and not at a time t=1020 ns or more thereafter.

It is a particular feature of the present invention that the concentration calculated by computer 256 based on the sensed absorption at one or more wavelength characteristic of an element of interest is employed directly, and without the need for any calibration, to provide a material directing output 281 to a material directing gate 282, which physically directs the materials 200 in one of at least two directions depending on the quantitative composition thereof.

Reference is now made to FIG. 1C, which is a simplified illustration of a system for classifying materials in real time while they are in motion in accordance with another preferred embodiment of the present invention. As seen in FIG. 1C, materials 300, such as ore taken from a mine, recycled materials, food or drugs on a manufacturing line, move along a conveyor 302, typically at a speed of 2-6 meters per second.

The present invention enables the materials 300 to be classified in real time in accordance with their quantitative composition. Thus, in the example of ore taken from a mine, the quantity of specific elements in the ore may determine whether and how the ore is further processed. For example, in the case of iron ore, if the iron oxide content is more than a predetermined threshold, typically 60%, the ore is further processed and if the iron oxide content is less than the predetermined threshold the ore is discarded. In another example, if phosphate ore is being classified, ore having a magnesium oxide content exceeding a predetermined threshold, typically 2%, is discarded and ore having a magnesium oxide content which is less than the predetermined threshold is further processed.

In accordance with a preferred embodiment of the present invention quantitative classification of materials 300 is achieved by employing a laser pulse generator operative to generate at least first and second laser pulses which impinge on the same impingement location on the materials 300 when they are in motion, the first and second laser pulses being separated in time by up to 10 microseconds. An absorption detector, typically including a spectrometer, is operative to sense an absorption spectrum at the impingement location over a detection time duration of up to 20 nanoseconds following the second laser pulse. Alternatively, plural photodetectors, operative in the nanosecond range and each being associated with a different wavelength filter, may be employed.

Impingement of the first and second laser pulses on materials 300 produces mutually nested plasmas having a characteristic absorption spectrum over a time duration of most preferably up to about 10 ns following the second laser pulse, which absorption spectrum is clearly indicative of quantitative composition of materials 200 at the impingement location thereon, as described hereinbelow in detail with reference to FIGS. 2A-3.

As seen in FIG. 1C, the laser pulse generator preferably includes first and second lasers 332 and 334, typically Nd:YAG lasers each having an energy output of between 50 and 200 mJoule per pulse, which output via a beam aligner 336. The lasers 332 and 334 together with the beam aligner 336 are together commercially available from Quantel, 2 bis avenue du Pacifique, BP23 91 941, Les Ulis CEDEX, France, under the trade name TWINS BSL. The beam aligner 336 is operative to mutually align beams from lasers 332 and 334 which are at different physical locations so that the beams are precisely coaxial to within micron tolerances.

Typically, the lasers 332 and 334 output at a wavelength of 1064 nm. It is appreciated that other wavelengths may alternatively be used. It is also possible that lasers 332 and 334 may operate at different wavelengths. Normally, lasers 332 and 334 operate at different output energy levels, with the second laser 334, which produces the second laser pulse, operating at an energy level which is 5-10 times higher than the energy level of the first laser 332, which produces the first laser pulse. As a theoretical alternative, a single laser could be used, if such a laser could produce two laser pulses within 10 microseconds of each other.

Coaxial beam outputs 338 of beam aligner 336 are preferably reflected by a mirror 340, such as an NT47-117 mirror, commercially available from Edmund Optics Inc., 101 East Gloucester Pike, Barrington, N.J. 08007-1380 USA, onto an optical module 342, typically comprising first and second lenses 344 and 346 whose characteristics are as follows: F1=+80 mm−216 mm, D1=50 mm and F2=+108 mm−52 mm, D2 50 mm.

Lenses 344 and 346 are preferably mounted on a variable distance mounting assembly 348 including a linear motor 350, which enables the position of the lenses 344 and 346, as well as the distance between the lenses 344 and 346, to be varied in response to a control signal 351 based on a material height input 352. Material height input 352 represents the height of a beam focus location 354 of the coaxial output beams 338 on the materials 300.

A computer 356 preferably governs the timing and other characteristics of the operation of first and second lasers 332 and 334 in order to provide desired timing and other operational characteristics of the corresponding first and second laser pulses and also provides control signal 351 in response to material height input 352 from a height sensor 358, such as an ultrasonic distance measuring device, for example a mic +130/IU/TC, commercially available from Microsonic GmbH of Hauert 16, 44227, Dortmund, Germany, or a laser rangefinder, such as an LDM 41/42 A, commercially available from ASTECH Angewandte Sensortechnik GmbH, Schonenfahrerstr. 5, D-18055, Rostock, Germany.

Optical module 342 is operative to focus the coaxial beam outputs 338 at the beam focus location 354 so as to preferably define a beam focus location having a diameter of approximately 300 microns. The beam focus location 354 is intended to be identical to the impingement location of each of the first and second laser beams on the materials 300, it being appreciated that a minor shift of up to about 10 microns in the impingement location on the materials 300 will exist due to movement of the materials 300 on the conveyor 302 between the times of the first and second laser pulse impingements. Impingement locations having a mutual center shift of no more than about 10 microns are considered to be the same impingement location.

Radiation from plasmas created on the materials 300 by impingement of the first and second pulses thereon is partially collected by a collected radiation focusing optical module 364, which focuses it at an end 366 of an optical fiber 367, which feeds it to a spectral analysis device 368, such as a Shamrock SR-303i-A spectrometer combined with a fast Andor ICCD camera DH720-25F-03, commercially available from Andor Technology plc., 7 Millennium Way, Springvale Business Park, Belfast, BT12 7AL, United Kingdom. The ICCD camera preferably has a gating window whose opening duration is preferably governed by a control signal 369 from computer 356.

The optical module 364 preferably comprises first and second lenses 370 and 372 whose characteristics are as follows: F1=+70 mm−116 mm, D1=50 mm and F2=+80 mm−52 mm, D2=50 mm.

Lenses 370 and 372 are preferably mounted on a variable distance mounting assembly 374 including a linear motor 376, which enables the position of the lenses 370 and 372, as well as the distance between the lenses 370 and 372, to be varied by control signal 351 from computer 356.

A spectral analysis output 380, typically as shown in FIGS. 2A-2C, from spectral analysis device 368 is preferably supplied to computer 356. FIGS. 2A-2C are a series of three, 3-dimensional intensity graphs, taken respectively at time periods t=0-900 ns, t=1000-1010 ns and t=1020-3000 ns, which are characteristic of analysis of lead ore in accordance with a preferred embodiment of the present invention. Each graph shows emission intensity as a function of both wavelength and time.

Computer 356 typically performs the following computational functions:

1. Calculates the Optical Density (O.D.) which is the logarithm (log) of the inverse intensity ratio between the minimum and the baseline adjacent thereto for each minimum in an intensity graph that represents an element of interest. For the purposes of illustration, reference is made to an intensity graph taken at t=1000 ns seen in FIG. 2B. The minimum is here designated by reference numeral 190 and the adjacent baseline is here designated by reference numeral 192. The intensity at the minimum 190 in this example is seen to be 10,000 while the intensity at the baseline 192 is seen to be 30,000. Thus the inverse of the ratio between the minimum and the baseline adjacent thereto is 3.0. The O.D. of the absorption at the wavelength which represents the specific element, here lead, is log 3 which equals 0.48.

It is a particular feature of the present invention that it employs the fact that the O.D. of the absorption spectrum at a wavelength which represents a given element is directly and linearly related to the quantitative concentration of the element, here lead, in the materials 300. The linear relationship is preferably represented as follows:

$$N_i = \frac{2.3}{l\sigma_i} OD_i$$

where $N_i$ is the concentration for an element designated by "i", l is the difference in the radius of the diameters of the plasma plumes created by impingement of the respective first and second laser beams and is typically 400 microns at t=1000 ns (FIGS. 2B & 3) and $\sigma_i$ is the absorption cross section given by the expression:

$$\sigma_i = A_{21} \frac{1}{8\pi} \lambda_{0i}^2 \frac{g_2}{g_1}$$

where $A_{21}$ is the Einstein coefficient for spontaneous emission for a specific energy level transition corresponding to the central wavelength, $\lambda_{0i}$ and $g_1$, $g_2$ are known constants representing the statistical weight of lower and upper energy levels to which the transition corresponds.

Referring to FIGS. 2A-2C, it is appreciated that a comparison of these graphs shows that absorbance is indicated only at and immediately following impingement of the second laser pulse on the materials 300, typically at t=1000 ns, and not prior thereto, and not at a time t=1020 ns or more thereafter.

It is a particular feature of the present invention that the concentration calculated by computer 356 based on the sensed absorption at one or more wavelength characteristic of an element of interest is employed directly, and without the need for any calibration, to provide a material directing output 381 to a material directing gate 382, which physically directs the materials 300 in one of at least two directions depending on the quantitative composition thereof.

Reference is now made to FIG. 3, which is a simplified illustration of aspects of the operation of the systems of FIGS. 2A, 2B & 2C. As seen in FIG. 3, an initial laser pulse, typically a Nd:YAG laser pulse at a wavelength of 1064 nm at a typical energy of 5 mJoule and typical duration 6-8 ns, impinges, at a time t=0, on a material while it is in motion typically at a speed of 2-10 meter/second, at an impingement location having a typical diameter of 300 microns, producing a plasma plume designated by letter A, having a typical emission pattern, typically at t=50 ns, symbolically shown at A1.

In accordance with a preferred embodiment of the present invention, a second laser pulse, typically a Nd:YAG laser pulse at a wavelength of 1064 nm at a typical energy of 50 mJoule and typical duration 6-8 ns, impinges, typically at a time t=1000 ns, on the material sample while it is in motion. The impingement location of the second laser pulse has a typical diameter of 300 microns. In accordance with a preferred embodiment of the present invention, the impingement location of the second laser pulse on the material generally overlaps the impingement location of the first laser pulse and the center of the impingement location of the second pulse has a center which typically is within 2-10 microns of the center of the impingement location of the first laser pulse.

The second laser pulse produces a plasma plume designated by letter B, having a typical emission pattern, typically at t=1000 ns, symbolically shown at B1.

In the meantime, plasma plume A expands as shown and has a typical emission pattern, typically at t=1000 ns, symbolically shown at A2.

It is a particular feature of the present invention that the total emission pattern of the combined plasma plumes A and B is detected at the time of the maximum intensity of the second laser pulse and within a detection window of between 0-10 ns, and more preferably 0-5 ns, thereafter. At this stage, l is typically 400 microns. This total emission pattern is shown symbolically at A2+B1 and includes sharp intensity drops which represent absorption of characteristic wavelengths of substances, preferably elements. The wavelengths and logarithms of ratios of intensities at the absorption peaks provide a clear indication of the quantitative composition of the material, as described in detail hereinabove.

FIG. 3 also shows that at a time approximately 10 ns following the second laser pulse, i.e. at approximately t=1010 ns, both of plasma plumes A and B continue to expand. Typical emission patterns for plasma plumes A, B and A+B at time t=1010 ns are symbolically shown at A3, B2 and A3+B2 respectively. It is seen that the absorption peaks are substantially smaller than at t=1000 ns.

FIG. 3 additionally shows that at a time approximately 20 ns following the second laser pulse, i.e. at approximately t=1020 ns, both of plasma plumes A and B expand further. Typical emission patterns for plasma plumes A, B and A+B at time t=1020 ns are symbolically shown at A4, B3 and A4+B3 respectively. It is seen that the absorption peaks are barely present.

In practice, the peak optical density calculated from the plasma emission intensities (PEI) measured at the wavelengths characteristic of the substances present in the material represents the absorbance characteristic of plasmas of such materials. A graph of PEI over time, which appears in FIG. 3, clearly shows that the PEI, and thus the signal to noise ratio and detection sensitivity, is highest for a given wavelength at the time of the second laser pulse and shortly thereafter, typically t=1000-1005 ns and decreases to nearly zero at t=1010 ns.

It will be appreciated by persons skilled in the art that the present invention is not limited by what has been particularly shown and described hereinabove. Rather the scope of the present invention includes both combinations and subcombinations of features recited in the claims as well as modifications thereof which would occur to a person of ordinary skill in the art upon reading the foregoing and which are not in the prior art.

The invention claimed is:

1. A system for classifying moving materials in real time, the system comprising:
   a laser pulse generator operative to generate at least first and second laser pulses which impinge on the same impingement location on said moving materials, said first and second laser pulses being separated in time by up to 10 microseconds; and
   an absorption detector operative to sense an absorption spectrum at said impingement location over a detection time duration of up to 20 nanoseconds following said second laser pulse.

2. A system for classifying moving materials in real time according to claim 1 and wherein said absorption detector is operative to sense an absorption spectrum at said impingement location over a detection time duration of up to 10 nanoseconds following said second laser pulse.

3. A system for classifying moving materials in real time according to claim 1 and wherein said absorption detector operative to sense an absorption spectrum at said impingement location over a detection time duration of up to 5 nanoseconds following said second laser pulse.

4. A system for classifying moving materials in real time according to claim 1 and also comprising:
   a real-time rangefinder measuring a current distance to said impingement location; and
   a distance responsive laser beam focuser operative in response to an output from said real-time rangefinder for adjusting the focus of said laser pulses in real time to be focused on said impingement location notwithstanding varying heights of said materials.

5. A system for classifying moving materials in real time according to claim 1 and also comprising:
   a real-time rangefinder measuring a current distance to said impingement location; and
   a distance responsive absorption detection focuser operative for adjusting the focus of said absorption detector in real time to be focused on said impingement location notwithstanding varying heights of said materials.

6. A system for classifying moving materials in real time according to claim 4 and also comprising:
   a distance responsive absorption detection focuser operative in response to said output from said real-time rangefinder for adjusting the focus of said absorption detector in real time to be focused on said impingement location notwithstanding varying heights of said materials.

7. A system for classifying moving materials in real time according to claim 1 and wherein said second laser pulse is generated at an energy level at least 5 times an energy level of said first laser pulse.

8. A system for classifying moving materials in real time according to claim 1 and wherein said second laser pulse is generated at an energy level 5-10 times an energy level of said first laser pulse.

9. A system for classifying moving materials in real time according to claim 1 and also comprising a beam aligner operative to align said first laser pulse and said second laser pulse.

10. A system for classifying moving materials in real time according to claim 1 and also comprising:
   a computer; and
   a material directing gate, said computer operative to receive an output from said absorption detector and to provide a material directing output to said material directing gate.

11. A method for classifying moving materials in real time comprising:
   generating at least first and second laser pulses which impinge on the same impingement location on said moving materials, said first and second laser pulses being separated in time by up to 10 microseconds; and
   sensing an absorption spectrum at said impingement location over a detection time duration of up to 20 nanoseconds following said second laser pulse.

12. A method for classifying moving materials in real time according to claim 11 and wherein said sensing an absorption spectrum at said impingement location occurs over a detection time duration of up to 10 nanoseconds following said second laser pulse.

13. A method for classifying moving materials in real time according to claim 11 and wherein said sensing an absorption spectrum at said impingement location occurs over a detection time duration of up to 5 nanoseconds following said second laser pulse.

14. A method for classifying moving materials in real time according to claim 11 and also comprising:
   measuring a current distance to said impingement location; and
   adjusting the focus of said laser pulses in real time to be focused on said impingement location notwithstanding varying heights of said materials.

15. A method for classifying moving materials in real time according to claim 11 and also comprising:
   adjusting the focus of said absorption detector in real time to be focused on said impingement location notwithstanding varying heights of said materials.

16. A method for classifying moving materials in real time according to claim 11 and wherein said generating at least first and second laser pulses comprises generating said second laser pulse at an energy level at least 5 times an energy level of said first laser pulse.

17. A method for classifying moving materials in real time according to claim 11 and wherein said generating at least first and second laser pulses comprises generating said second laser pulse at an energy level 5-10 times an energy level of said first laser pulse.

18. A method for classifying moving materials in real time according to claim 11 and wherein said generating at least first and second laser pulses comprises aligning said first laser pulse and said second laser pulse.

19. A method for classifying moving materials in real time according to claim 11 and also comprising providing a material directing output based on a function of said absorption spectrum.

* * * * *